US009744001B2

(12) United States Patent
Choi et al.

(10) Patent No.: US 9,744,001 B2
(45) Date of Patent: Aug. 29, 2017

(54) DENTAL APPLIANCE WITH CAVITY FOR AN UNERUPTED OR ERUPTING TOOTH

(71) Applicant: Align Technology, Inc., San Jose, CA (US)

(72) Inventors: Jeeyoung Choi, Sunnyvale, CA (US); Chunhua Li, Cupertino, CA (US); John Morton, San Jose, CA (US); Bastien Pesenti, San Jose, CA (US); Vadim Matov, San Jose, CA (US); Alexander Beliaev, Moscow (RU); Petr Ushanov, Khmiki (RU); Roman A. Roschin, Moscow (RU)

(73) Assignee: Align Technology, Inc., San Jose, CA (US)

( * ) Notice: Subject to any disclaimer, the term of this patent is extended or adjusted under 35 U.S.C. 154(b) by 189 days.

(21) Appl. No.: 14/541,021

(22) Filed: Nov. 13, 2014

(65) Prior Publication Data
US 2016/0135924 A1    May 19, 2016

(51) Int. Cl.
*A61C 7/08*    (2006.01)
*A61C 7/00*    (2006.01)

(52) U.S. Cl.
CPC ............... *A61C 7/002* (2013.01); *A61C 7/08* (2013.01)

(58) Field of Classification Search
CPC ................................ A61C 7/002; A61C 7/08
USPC .......................................................... 433/6
See application file for complete search history.

(56) References Cited

U.S. PATENT DOCUMENTS

| 7,294,141 B2 | 11/2007 | Bergersen |
| 7,637,740 B2 | 12/2009 | Knopp |
| 8,099,268 B2 | 1/2012 | Kitching et al. |
| 8,275,180 B2 | 9/2012 | Kuo |
| 8,401,826 B2 | 3/2013 | Cheng et al. |
| 2003/0224312 A1 | 12/2003 | Bergersen |
| 2003/0224314 A1 | 12/2003 | Bergersen |
| 2008/0293003 A1 | 11/2008 | Moss et al. |
| 2008/0294405 A1* | 11/2008 | Kitching .................. A61C 7/08 703/11 |

OTHER PUBLICATIONS

"What is Ortho-Tain®?" OrthoTain™, A World Leader in Orthodontic Appliances, http://www.orthotain.com/what-is-ortho-tain®/, accessed Jul. 2, 2014, 2 pp.
(Continued)

*Primary Examiner* — Paula J Stice
(74) *Attorney, Agent, or Firm* — Brooks, Cameron & Huebsch, PLLC

(57) ABSTRACT

A method includes to receive, via a computing device, data representing a plurality of teeth, identify data indicating which of the plurality of teeth are unerupted or erupting, predict at least one characteristic of a tooth of the unerupted or erupting teeth after they have fully erupted using one or more tooth eruption prediction factors, generate new data representing the unerupted or erupting teeth in multiple states of eruption based upon the predicted at least one characteristic of the fully erupted teeth, and generate a series of incremental tooth arrangements with the new data to define a proposed orthodontic treatment based on the new data representing the unerupted or erupting teeth in multiple states of eruption.

7 Claims, 9 Drawing Sheets

(56) References Cited

OTHER PUBLICATIONS

Nourallah et al., "New Regression Equations for Predicting the Size of Unerupted Canines and Premolars in a Contemporary Population," Angle Orthod 2002: 72:216-221.
Paredes et al., "A New, Accurate and Fast Digital Method to Predict Unerupted Tooth Size," Angle Orthod 2006; 76:14-19.
Bernabe et al., "Are the Lower Incisors the Best Predictors for the Unerupted Canine and Premolars Sums? An Analysis of Peruvian Sample," Angle Orthod 2005; 75: 202-207.
Martinelli et al., "Prediction of Lower Permanent Canine and Premolars Width by Correlation Methods," Angle Orthod 2005; 75: 805-808.
International Search Report and Written Opinion from related PCT Application No. PCT/IB2015/002134, dated Jun. 1, 2016, 19 pp.
International Search Report and Written Opinion from related PCT Application No. PCT/IB2015/002134, dated Nov. 2016, 22 pp.

\* cited by examiner

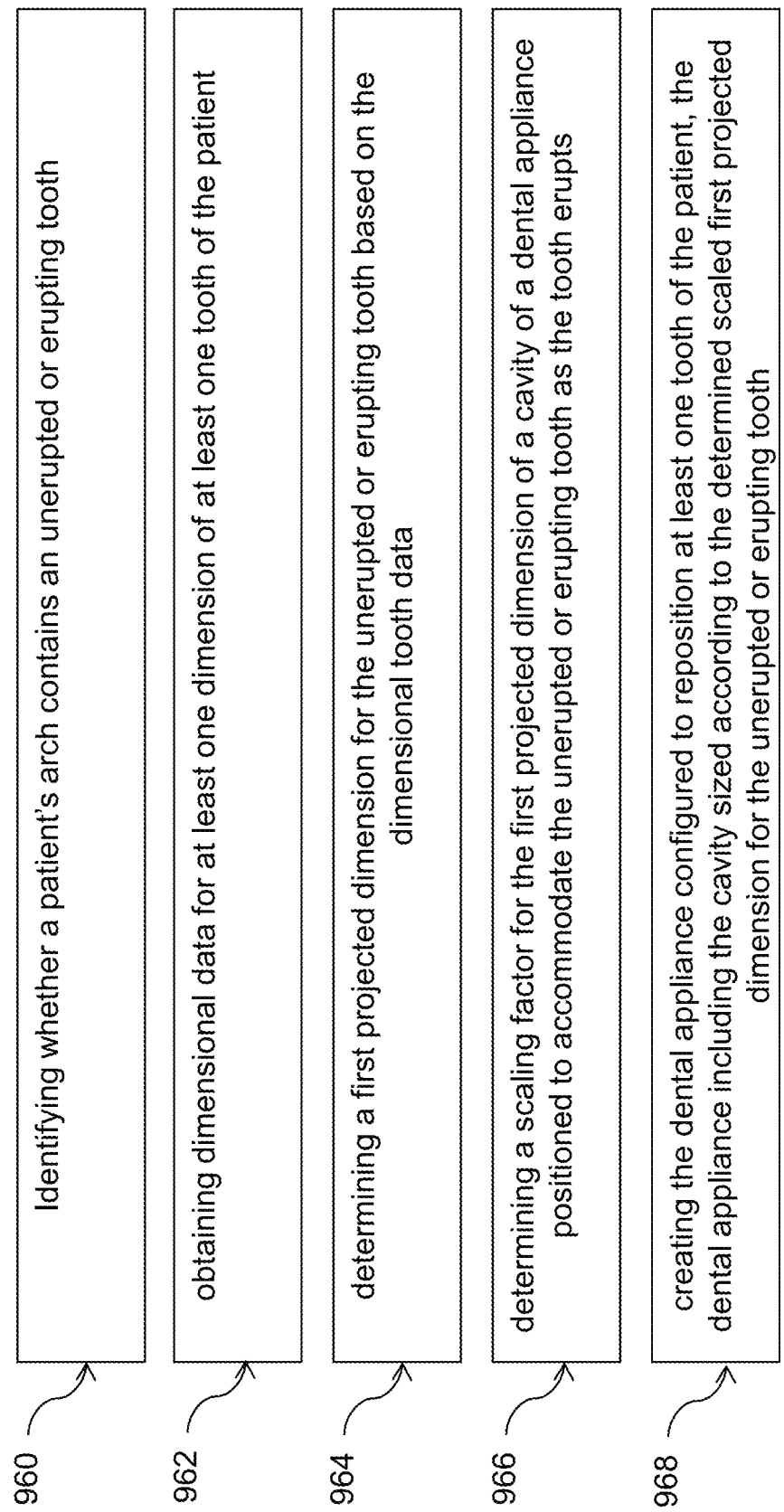

DENTAL APPLIANCE WITH CAVITY FOR AN UNERUPTED OR ERUPTING TOOTH

BACKGROUND

The present disclosure is related generally to the field of dental treatment. More particularly, the present disclosure is related to systems, methods, computing device readable media, and devices for creating a dental appliance having a cavity for an unerupted or erupting tooth.

Dental treatments may involve, for instance, restorative and/or orthodontic procedures. Restorative procedures may be designed to implant a dental prosthesis (e.g., a crown, bridge inlay, onlay, veneer, etc.) intraorally in a patient. Orthodontic procedures may include repositioning misaligned teeth and changing bite configurations for improved cosmetic appearance and/or dental function. Orthodontic repositioning can be accomplished, for example, by applying controlled forces to one or more teeth over a period of time.

As an example, orthodontic repositioning may be provided through a dental process that uses positioning dental appliances for realigning teeth. Such appliances may utilize a thin shell of light weight and/or transparent material having resilient properties, referred to as an "aligner," that generally conforms to a user's teeth but is slightly out of alignment with a current tooth configuration.

An example of orthodontic repositioning that can occur through a dental process is a process that uses one or more positioning dental appliances for realigning teeth. Placement of an appliance over the teeth can provide controlled forces in specific locations to gradually move the teeth into a new configuration. Repetition of this process with successive appliances in progressive configurations can move the teeth through a series of intermediate arrangements toward a final desired arrangement.

In some applications, one or more teeth may not have fully emerged from the gingiva into their final position in the patient's mouth. This process is often referred to as eruption of a tooth. As used herein, a tooth that has not emerged from the gingiva is referred to as not erupted, a tooth that has emerged from the gingiva and is moving toward its final position is referred to as partially erupted, and a tooth in its final position, when discussing eruption, is referred to herein as fully erupted.

Such dental appliances have cavities formed in the shell of the appliance into which one or more teeth will be positioned. Further, dental appliances used as aligners rely on resilient properties of the aligner material to impart force on one or more teeth to move the teeth and as such a space in the shell for an erupting tooth has to be provided for the shell and also has to be designed to provide whatever force is desired by the treatment plan. Therefore, design of the space on the shell cannot be done in a trivial manner.

When designing dental appliances for patients with erupting teeth, it can be difficult to provide an appropriately shaped appliance when little or nothing may be known about the tooth that is emerging or has yet to emerge. For example, orthodontic patients at growing ages often start their treatment when permanent canines and/or bicuspids are not fully erupted.

Natural eruption of these teeth is utilized to erupt the teeth. This process provides enough space in the arch and prevents interference with aligner structure during eruption, since even small magnitude of consistent or repeated force can impede or stop eruption.

Further, in some instances, the cavity for the erupting tooth may be sized incorrectly for the erupting tooth (e.g., based upon the space within the patient's mouth prior to the tooth erupting or in the early stages of eruption). Additionally, it may be difficult to predict the speed at which the tooth may erupt and, therefore, the shell may be designed such that it does not accommodate the tooth properly as it erupts. In some such instances, the tooth may contact one or more surfaces of the cavity which may slow the eruption process, cause discomfort to the patient, and/or unintentionally change the positioning of the appliance, among other possible issues.

BRIEF DESCRIPTION OF THE DRAWINGS

FIG. 9 illustrates an example of a method embodiment of the present disclosure for creating a dental appliance having a cavity for an unerupted or erupting tooth.

DETAILED DESCRIPTION

Figure 1:
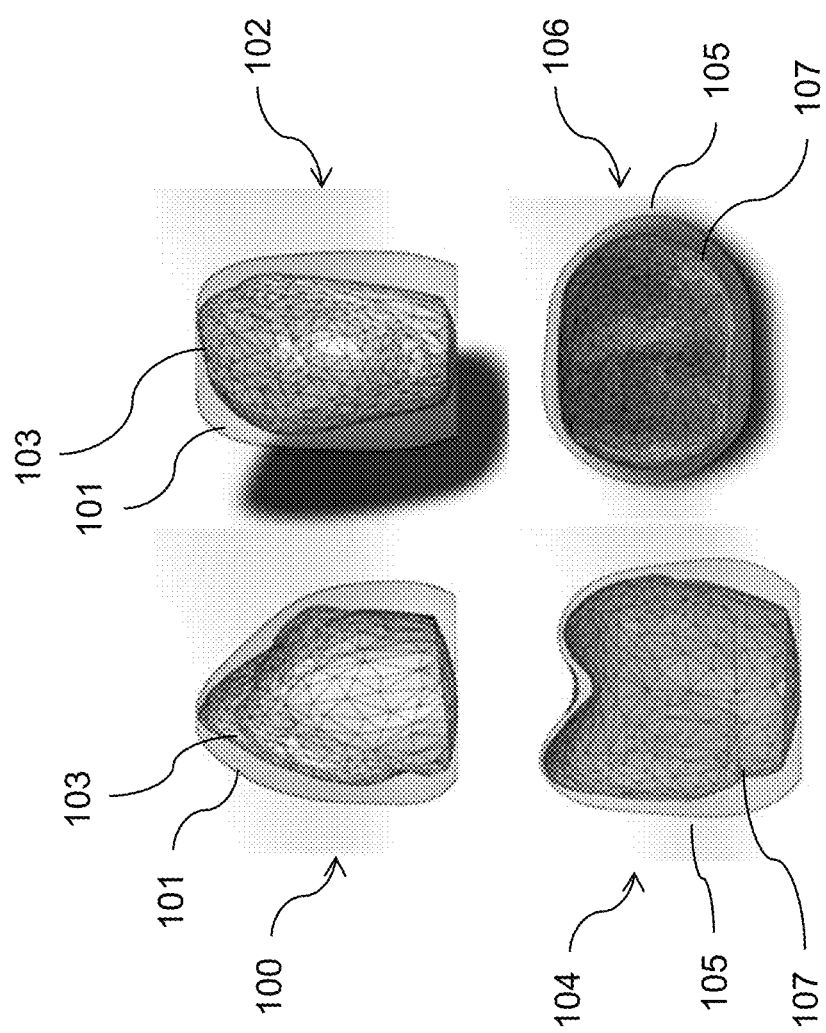
FIG. 1 illustrates examples of virtual geometries of several types of teeth according to one or more embodiments of the present disclosure.

The present disclosure is related to systems, methods, computing device readable media, and devices for creating a dental appliance having a cavity for an unerupted or erupting tooth. Currently, some of the most often heard clinical barriers for teen utilization of dental appliances are the challenges due to unerupted teeth.

Doctors have a hard time predicting eruption time, rate, size of the tooth, orientation, and/or location during the course of a dental treatment process. Embodiments of the present disclosure can more closely predict tooth dimension and/or position. Embodiments of the present disclosure also can utilize a bubbled space to form a cavity in the shell of the device for placement of the erupting tooth to better ensure natural eruption with reduced or minimized potential interference with surfaces of the dental appliance. However, it is not just about making the cavity bigger, the cavity has to be sized to be accommodated by the other items around the cavity (e.g., adjacent teeth, gingiva, teeth of the opposing jaw, the tongue of the patient, etc.).

Such features can lessen a treatment professional's concerns of eruption during treatment, among other benefits. Reducing the above mentioned clinical barrier for teen utilization can enable treatment professionals to treat more patients. Also, current virtual geometry analysis may require a treatment professional to manually adjust the model of the patient's teeth, which can result in treatment inconsistency. Embodiments of the present disclosure include embodiments that can be largely based on an automated procedure thus reducing technician process time and maximizing protocol consistency.

The present disclosure also includes device embodiments. For example, in some embodiments, the device is appliance designed to implement at least a portion of a treatment plan, comprising a shell having a plurality of cavities therein designed to receive teeth of a jaw with at least one of the plurality of cavities being a cavity for accommodating an unerupted or erupting tooth therein, wherein at least one of a size, shape, location, and orientation of at least one of the cavities for accommodating an unerupted or erupting tooth are based upon a prediction of at least one of a size, shape, location, or orientation of the unerupted or erupting tooth.

Additionally, embodiments of the present disclosure can include system embodiments wherein multiple dental appliances can be used in sequence to move one or more teeth according to a treatment plan developed by a treatment professional. For example, in some embodiments, the dental appliance system can include a first appliance of a series of appliances designed to incrementally implement a treatment plan, comprising a first shell having a plurality of cavities therein designed to receive teeth of a jaw in a first stage of the treatment plan with at least one of the plurality of cavities being a cavity for accommodating an unerupted or erupting tooth therein.

The system can also include a second appliance of the series of appliances, comprising a second shell having a plurality of cavities therein designed to receive teeth of the jaw in a second stage of the treatment plan the second shell having a cavity that corresponds with the cavity for accommodating an unerupted or erupting tooth of the first shell and wherein the cavities for accommodating an unerupted or erupting tooth are sized, shaped, located, and/or oriented based upon a prediction of the size, shape, location, and/or orientation of the unerupted or erupting tooth according to each shell's respective treatment stage. In this manner, as one or more of the teeth erupt, the cavities of the shell can be adjusted to more accurately fit each tooth as it erupts.

In various embodiments, the cavities for accommodating an unerupted or erupting tooth each differ in at least one tooth eruption prediction factor (e.g., size, shape, location, and orientation). This can be accomplished, for example, by utilizing data representing the unerupted or erupting teeth in multiple states of eruption that is based upon the predicted size, shape, location, and/or orientation of the fully erupted teeth to adjust one or more of the size, shape, location, and orientation of the cavity.

At least one of the size, shape, location, and orientation can also be determined and/or adjusted based upon other tooth eruption prediction factors, as discussed in more detail herein. For example, the cavities for accommodating an unerupted or erupting tooth can be sized, shaped, located, and oriented based on data including: a size, shape, location, and orientation of a tooth adjacent to the unerupted or erupting tooth and/or based on data including: a size, shape, location, and orientation of an opposing tooth (i.e., a tooth on the opposing jaw of the patient that may interact with the unerupted or erupted tooth) to the unerupted or erupting tooth. The cavities for accommodating an unerupted or erupting tooth can also, alternatively or additionally be sized, shaped, located, and/or oriented based on data including: a size, shape, location, and/or orientation of a tooth that is the same type of tooth as the unerupted or erupting tooth (i.e., canine, premolar, etc.).

In some embodiments, the cavities for accommodating an unerupted or erupting tooth include a gingival edge and wherein the gingival edge is located and shaped based upon a prediction of the location and shape of the gingiva that will be adjacent to the gingival edge according to each shell's respective treatment stage. In this manner, the cavity gingival edge location and shape can be adjusted to provide more specialized force characteristics due to the adjustability between dental appliances. For example, as a tooth emerges during the stages of a treatment plan in which dental appliances are used, the gingival edge of each appliance can be shaped different to accommodate the different shape of the gingiva as the tooth emerges from it.

In some such embodiments, a predicted characteristic, such as the predicted orientation of the erupting tooth can be made more precise, for example, by using additional information from the patient, such as, for example, if the crown and/or root of the erupting tooth is visible from a 2-dimensional (2D) scanning technique, such as an x-ray image, (e.g., the long axis orientation of the erupting tooth could be measured in the plane of the x-ray image), this information could be used as a predictor of the orientation of the crown of the erupting tooth.

In another example, if the crown of the erupting tooth or the root is visible from the output of a 3-dimensional (3D) scanning technique, such as Cone Beam Computed Tomography (CBCT), a characteristic can be predicted. For example, the long axis orientation of the erupting tooth could be measured in three dimensions, relative to the adjacent neighboring teeth that are visible the virtual treatment data. Then, this information could be used as a predictor of a characteristic, such as the orientation of the crown of the erupting tooth.

There are also many other aspects of the embodiments of the present disclosure that will be discussed in more detail below, in reference to the examples provided in the drawings. In the following detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice the embodiments of this disclosure, and it is to be understood that other embodiments may be utilized and that process and/or structural changes may be made without departing from the scope of the present disclosure. As used herein, "a number of" a particular thing can refer to one or more of such things (e.g., a number of forces can refer to one or more forces).

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention, and should not be taken in a limiting sense.

FIG. 1 illustrates examples of virtual geometries of several types of teeth according to one or more embodiments of the present disclosure. In the embodiment illustrated in FIG. 1, a number of tooth anatomies (e.g., ten, twenty, onehundred, etc.) were selected and were compared to each other (e.g., overlaid over each other) to create a tooth shape (a generic dimensional tooth design) that includes that maximum possible dimensions of the target tooth. For example, a first tooth shape has a particular shape and when compared to a second tooth, of the same type, the second tooth will have a different shape with a different outer contour in multiple dimensions such that it may, for example have a larger mesiodistal (MD) length than the first tooth, but a smaller buccolingual (BL) length.

In such an embodiment, the comparison can overlay the two data sets and take the data points that are furthest from a reference point (e.g., a center point in the tooth) to create a tooth shape that is the maximum dimensions of the two combined data sets. This methodology can be accomplished with data sets of more than two teeth (e.g., tens, hundreds, thousands, millions, etc. of data sets of teeth can be used).

This created generic dimensional tooth design information can be used for each target tooth to aid in predicting at least one of the size, location, shape, and/or orientation of the target tooth and to provide a general tooth shape that can be utilized for any patient's target tooth.

The anatomies can be provided from a variety of resources. For example, anatomies can be provided from other patient cases, one or more pontic galleries, typodonts, and/or other teeth of the patient, among other resources. Further, the selection can, for example, be made automatically (e.g., based upon computing executable instructions that compare the anatomies to each other, as discussed above, and/or to a predicted shape, size, location, and/or orientation of the unerupted or erupting tooth based on the compared anatomies) or by a treatment professional of computing device operator.

From these selections, a generic dimensional design that envelops the outermost surface of the overlaid geometries can be created, as discussed above. The generic envelope can, for example, be represented as a custom-designed parametric 3D surface model, approximating tooth geometry. For instance, in some simpler embodiments, the generic surface is a fixed, custom-designed geometric shape, and parameters allow for scaling each dimension (e.g., mesiodistal, buccolingual, coronal-apical) independently. In other embodiments, the surface may be represented by a set of parametric surfaces (e.g., non-uniform rational B-splines). In such embodiments, control points and any other parameters of the surface can, for instance, be adjusted to approximate the outermost surface of the overlaid geometries.

In other embodiments, such as that illustrated in the embodiment of FIG. 1, two tooth envelopes (i.e., tooth envelopes with a tooth 100 and 102 show a first envelope 101 around a canine tooth 103 and tooth envelopes with a tooth 104 and 106 show a second envelope 105 around a bicuspid tooth 107) are shown from two perspectives. In some embodiments, this information can be displayed, such as on a display of a computing device, as illustrated in FIG. 1. However, in some embodiments, the information is data that is used within the process of creating one or more dental appliances and is not displayed.

The outermost surface of the overlaid geometries creates an envelope that is a bubble-like form 101 that represents the maximum extent to which a tooth should extend outward from a reference point in three dimensions (at least, based upon the selected anatomies used in the calculation above). In this manner, a dental appliance cavity having a size, shape, location, and/or orientation similar to that of the bubble-like form with respect to that particular tooth type should not contact any surface of the erupting tooth. Embodiments of the present disclosure can take this information into account when designing the dental appliances.

Figure 2:
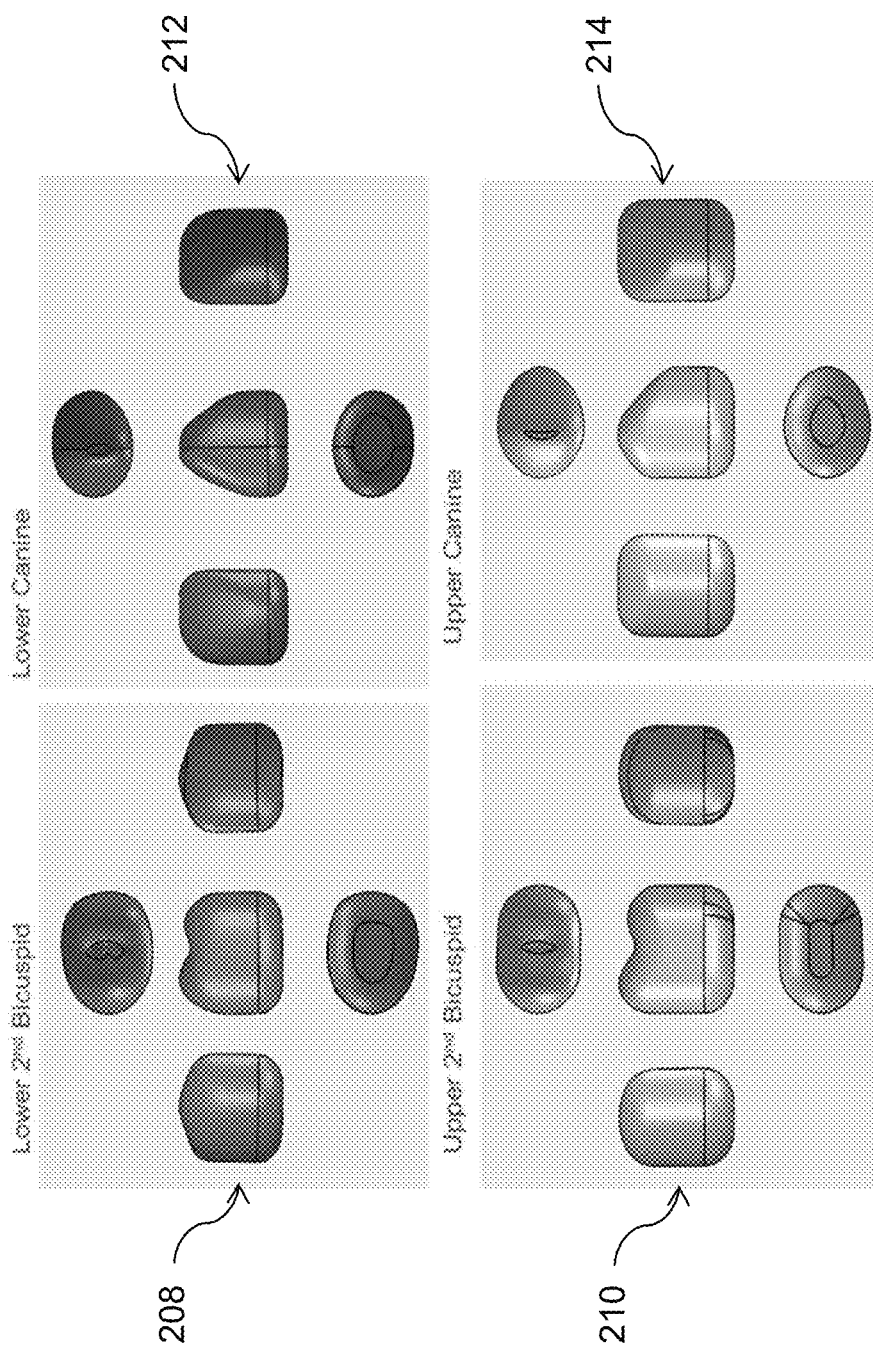
FIG. 2 illustrates examples of standard virtual geometries of several types of teeth that can be created according to one or more embodiments of the present disclosure.

From this calculation of one or more of the predicted tooth shapes, locations, orientations, and sizes and the potential bubble-like forms, one or more standard geometries can be created, as discussed in more detail with respect to FIG. 2. FIG. 2 illustrates examples of standard virtual geometries for several types of teeth that can be created according to one or more embodiments of the present disclosure. Shown in FIG. 2 are shapes based on the generic dimensional design information, for example, from FIG. 1. The shapes in FIG. 2 are designed to universally envelop the maximum data points from a reference point in a comparison of multiple data sets.

In some embodiments, the virtual geometry shape of the tooth and/or the bubble can be made more precise, using additional information from the patient of the target tooth. For example, if the crown of the unerupted or erupting tooth is visible from a 2D scanning technique (e.g., an x-ray image), the mesiodistal and coronal-apical size of the crown can be measured in the x-ray image, (e.g., proportionally to one or more neighboring fully-erupted teeth and used to compute the size of the geometry of the tooth to be erupted). This patient specific information can be used to modify the generic dimensional design shape to make the shape more precise to the patient's mouth.

For example, the size could be measured manually and entered in the software by a user, it could be detected semi-automatically by selected one or more landmark points (e.g., four points: mesial, distal, coronal, and apical could be selected and then the process could be done automatically, via computing device executable instructions using these points) on an unerupted or erupting tooth crown and neighboring teeth, or could be detected automatically, for example, by contour detection and other image processing techniques and this information could be used in creating the generic dimensional design and/or modifying a generic dimensional design shape created from non-patient data sets.

In a further example, if the crown of the erupting tooth that has not emerged from the gingiva is visible from the output of a 3D scanning technique, such as CBCT, the crown surface of the unerupted tooth could be reconstructed partially or completely. In case of a partial reconstruction, the crown could, for example, be completed using generic crown data (for an example of generic crown data, see U.S. Pat. No. 7,865,259). Then, the size of the crown to be erupted can be measured from the reconstructed 3D data. In addition, the 3D shape of the virtual geometry to be reconstructed can be derived from the scanned geometry. Such methods can be complementary to or used as an alternative to a tooth size regression model as discussed elsewhere herein.

In the examples of FIG. 2, standard virtual geometries are shown for four tooth types. Geometry 208 represents a lower $2^{nd}$ bicuspid, geometry 210 represents an upper $2^{nd}$ bicuspid, geometry 212 represents a lower canine, and geometry 214 represents an upper canine.

As these geometries were created by utilizing data from multiple, and in some cases many, tooth anatomies, these standard virtual geometries may be able to be utilized on a tooth of that type in many patients. In patients in which such standard geometries may not fit or where further precision is desired, further refinement processes are discussed in more detail herein. The geometries shown represent a bubble-like form that can be used to determine that shape of a cavity to be formed within a shell of a dental appliance.

Figure 3:
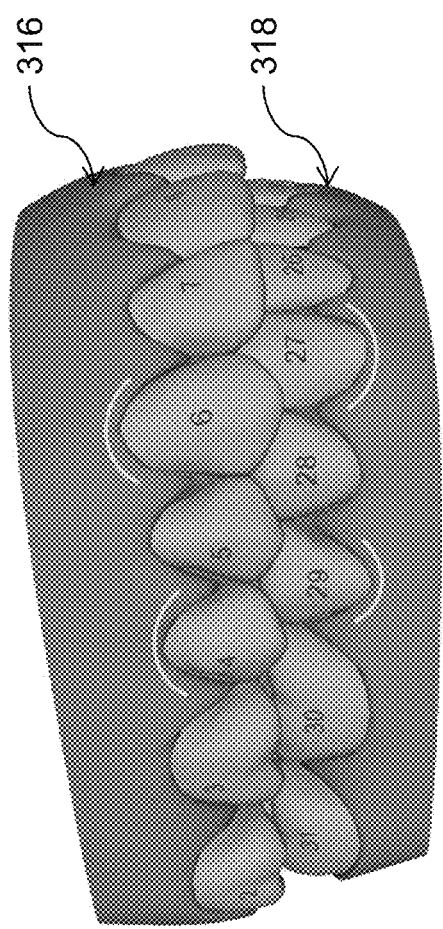
FIG. 3 illustrates an example view of a portion of a virtual model of an upper jaw and lower jaw of a patient that can be used in creating an appliance according to one or more embodiments of the present disclosure.

FIG. 3 illustrates an example view of a portion of a virtual model of an upper jaw and lower jaw of a patient that can be used in creating an appliance according to one or more embodiments of the present disclosure. As discussed herein, one or more of the neighboring teeth can be used to help predict the size, shape, location, and/or orientation of an unerupted or erupting tooth. For example, if the unerupted or erupting tooth is in tooth position #6 on the upper jaw 316, then one or more teeth in positions #5 and #7 (adjacent teeth) and #27 and #28 (opposing teeth) can be utilized.

Additionally, a tooth in another part of the mouth that has already erupted (partially or fully) that is of the same tooth type can be utilized, in some embodiments. For example, if one upper canine is unerupted, but the other canine tooth, sometimes referred to as a "counterpart tooth", has erupted, one or more of the tooth eruption prediction factors may be present in the counterpart tooth (e.g., the characteristics: size, location, shape, and/or orientation) which can be used to predict the size, shape, location, and/or orientation of the erupting or unerupted tooth, alone or in combination with one or more neighboring teeth of an unerupted or erupting tooth.

As discussed above, in some embodiments, the expected dimensions of a partially-erupted or unerupted tooth can be extrapolated from the known characteristics of one or more neighboring teeth (adjacent, opposing, and/or counterpart tooth). For instance, one or more of the tooth eruption prediction factors, such as, Buccolingual (BL) widths and/or Mesiodistal (MD) widths of partially erupted or fully erupted neighboring teeth can be used as regressors in a multivariate regression model, as discussed in more detail below. Such an analysis can, for example be used in a tooth size prediction.

Figure 4:
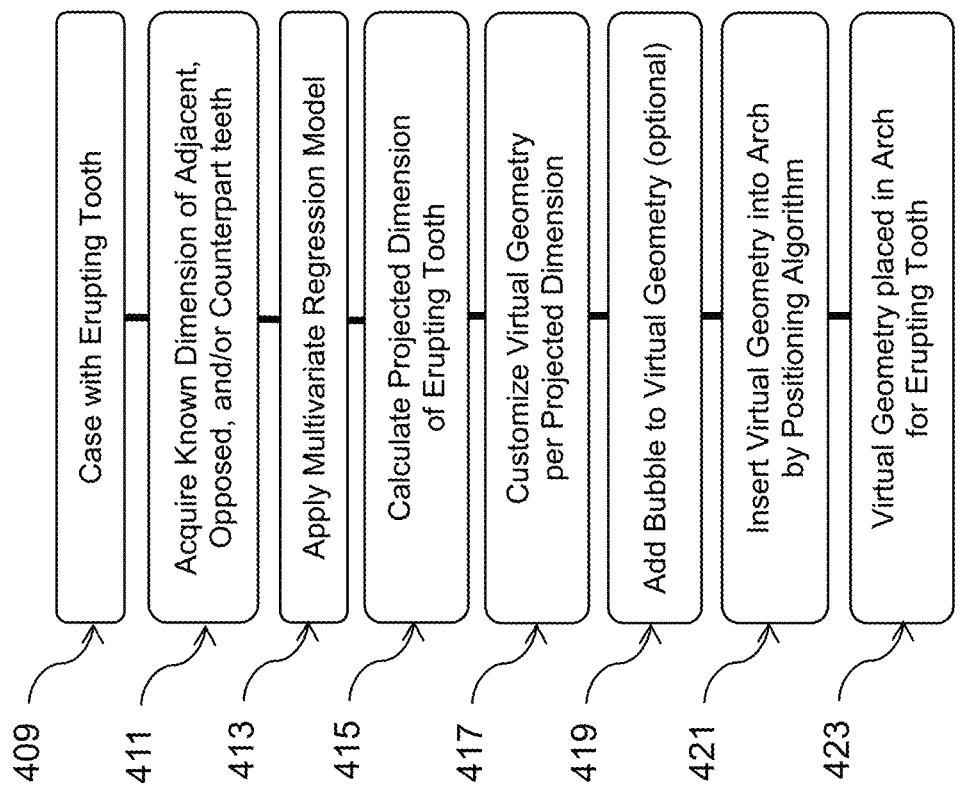
FIG. 4 illustrates an example of a process for treatment planning of the present disclosure.

FIG. 4 illustrates an example of a process for treatment planning of the present disclosure. In this example, the case is first checked to determine whether or not the patient has erupting teeth at 409. If the patient does have erupting teeth, those one or more teeth are identified. These processes can be accomplished by executable instructions that, for example, check tooth size, location, shape, and/or orientation to determine substantial matches to the size, location, shape, and/or orientation of a tooth in a typodont, pontic gallery or a standard virtual geometry, as discussed herein.

In the embodiment of FIG. 4, the method analyzes the data of the counterpart, adjacent, and/or opposing teeth to determine at least one dimension (e.g., X, Y, and/or Z dimension data in a three dimensional coordinate system) of each of the counterpart, adjacent, or opposing teeth to be utilized in the prediction of the size, shape, location, and/or orientation of the erupting or unerupted tooth and/or the size, shape, location, and/or orientation of the cavity to be created on the shell of one or more dental appliances at 411.

In some embodiments, such as that shown in the embodiment of FIG. 4, a multivariate regression model or other suitable model, such as others described herein can be utilized to further refine the dimension of the erupting or unerupted tooth and/or the size, shape, location, and/or orientation of the cavity to be created on the shell of one or more dental appliances at 413. This type of model can, for example, be utilized where there are multiple adjacent, opposite, or counterpart teeth that are being used in such analysis.

For instance, multiple teeth can be used in a prediction model. In such an implementation, the number of teeth to be used in modeling can, for example, be identified, a model that can use that number of teeth can be selected, the regression process can be applied to the tooth data through use of the selected regression model. This analysis can be used to determine one or more projected tooth dimensions as illustrated in FIG. 4.

In some embodiments, one or more standard virtual geometry and/or pre-defined virtual geometry (e.g., from pontic gallery, partially erupted or fully erupted counterpart tooth) dimensions, for example, as discussed with respect to FIGS. 1 and 2 above, can be customized to match the one or more projected tooth dimensions. Once such a virtual geometry is selected, data can be used to determine how to scale the virtual geometry size up or down to better fit with the size of the teeth of the patient. In some embodiments, a scaling factor can be applied to one or more virtual geometry dimensions to match the one or more projected tooth dimensions or create a bubbled virtual geometry. A scaling factor can be used to scale a dimension up or down. For example, in order to ensure that the erupting tooth does not contact a surface of the cavity, a Z dimension of the projected tooth dimensions could be scaled up such that the tooth would not extend that far from the patient's gingiva or other reference point.

In some embodiments, each dimension could be scaled differently. For example, the X dimension scaled up by 5%, the Y dimension by 3%, and the Z dimension by 7%. In some embodiments, a scaling factor can also be applied to one or more of the standard virtual geometry dimensions. This can be done to change the dimensions of virtual geometries from various sources before they are compared to the projected dimensions of the erupting or unerupted tooth or to adjust the virtual geometry dimensions so that their dimensions will be different going forward as applied to the next patient.

These various processes can be used to calculate one or more projected dimensions of the target tooth (e.g., as illustrated at 415) and to create a customized virtual geometry for a particular tooth of a particular patient, and/or at a particular time in a treatment process, for example as shown at 417. Alternatively or additionally, a bubbled virtual geometry can also be calculated (e.g., at 419 of FIG. 4), in some embodiments. In these ways, each patient may have a customized fit for their dental appliances based on the individualized analysis done utilizing one or more of the processes described above.

As illustrated in FIG. 4, the virtual geometry can then be inserted into a virtual model of the patient's jaw for planning of the movement of the teeth of the patient and/or design of one or more dental appliances, as shown at 421. The virtual geometry can then be positioned and oriented to provide a treatment plan for treating the patient based on the modified geometry provided by the embodiments of the present disclosure, as illustrated at 423.

In various embodiments, the number of regressors and/or models can vary depending on the availability of partially or fully erupted neighboring teeth. For example, 5-regressor model can be chosen if two adjacent teeth, two opposing teeth, and the counterpart tooth on the other side of the patient's arch are all fully erupted.

A 3-regressor model could be selected if, for example, two adjacent teeth and one opposing tooth are fully erupted. Then, a standard virtual geometry that has been refined based on such a regression can be scaled up/down accordingly to contain the projected unerupted tooth with an appropriately sized and shaped bubbled space. As discussed herein, the scaling can be different for different dimensions of the virtual geometry.

Bubble thickness for each virtual geometry can be constant or varying, for example, in MD and BL directions. All of the numerical calculations including expected tooth dimension and/or scaling factor can be automated (e.g., via executable instructions) in order to reduce or minimize manual adjustment by treatment professionals or computing device operators and to improve treatment protocol consistency, among other potential benefits. Embodiments that create virtual geometries of a customized tooth size with a bubbled space can, for example, minimize potential size mismatch of virtual geometries with the real tooth during/after eruption, among other potential benefits.

In some embodiments, a placed virtual geometry, (especially those with a bubbled geometry) might collide with a tooth (e.g., virtual geometry) in the opposing arch (i.e., an inter-arch collision), which could result in an open bite (where the jaws do not mate or close fully) upon occlusion. One solution for this is to reshape the virtual geometry by removing the volume of the cavity that will collide with the opposing arch.

The volume can, for example, be dynamically adjusted according to the staged position of the opposing teeth during the treatment to ensure desired occlusion. The volume to be removed, can be identified by, for example, in a virtual model, moving the jaws to a fully closed position and then reviewing the data to identify where teeth may be overlapping. Once overlapped areas are identified, modifying the virtual geometry in one or more dimensions to remove any overlapping areas and/or modifying one or more surfaces to better mate the surfaces of opposing teeth together.

Figure 5:
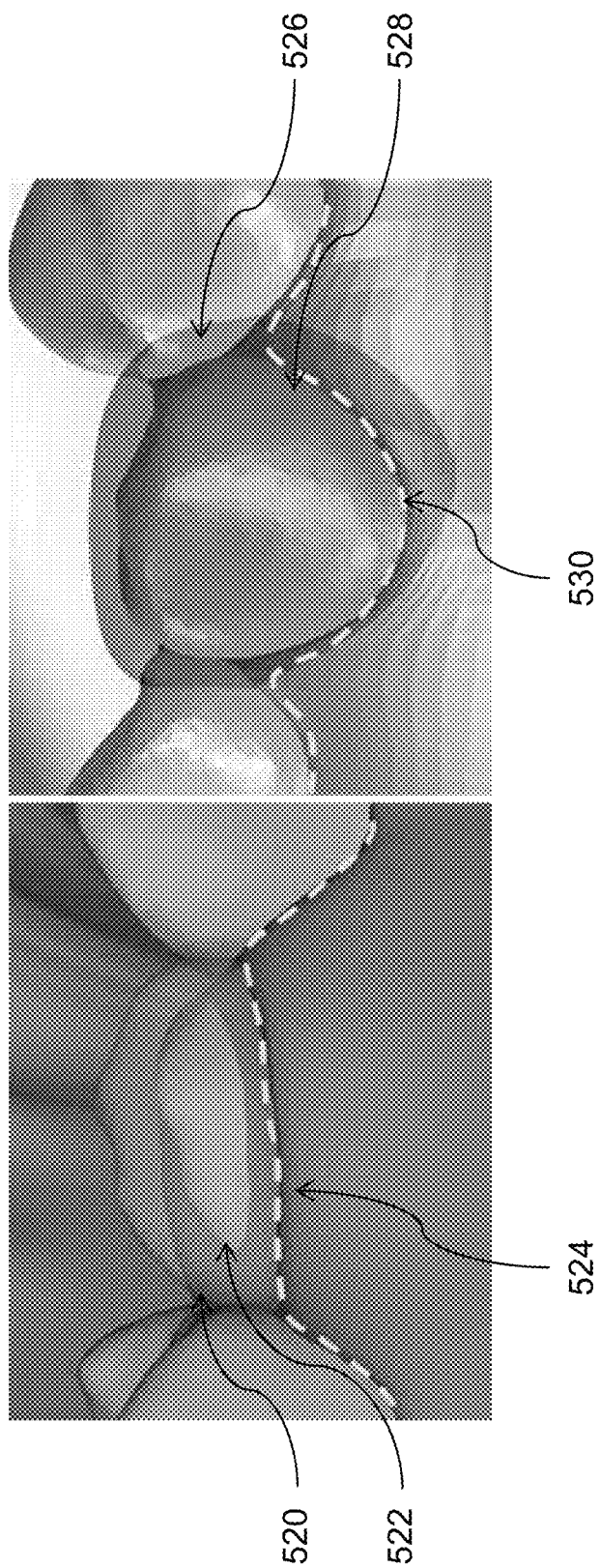
FIG. 5 provides an example of a prior art cavity for an erupting tooth in the left image and an example of a cavity for an erupting tooth according to one or more embodiments of the present disclosure in the right image.

FIG. 5 provides an example of a cavity for an erupting tooth in the left image and an example of a cavity for an erupting tooth according to one or more embodiments of the present disclosure in the right image. As discussed above, in some embodiments, the gingival edge (e.g., 524 and 530 of the images of FIG. 5) of the dental appliance can be shaped to provide greater force distribution to the rest of the appliance, among other benefits. In devices, such as that shown in the left image of FIG. 5, gingival edge 524 for virtual geometries is, in many cases, virtually bypassed which can result in a short crown height of the cavity 520 in manufactured aligners. The goal of such implementations is to prevent unwanted contact with erupting tooth 522.

In embodiments of the present disclosure, the gingival edge 530 of the cavity 526 having the erupting tooth 528 therein can be shaped similarly to when the tooth is fully erupted and thus aligner mechanical integrity is not compromised and there are fewer chances for distortion and breakage. In some embodiments, the gingival edge can be adjusted from one appliance to a subsequent appliance worn during a later stage in treatment as the tooth continues to erupt and, therefore, one or more appliances in a series of appliances for implementing a treatment plan may have differently shaped gingival edges.

Figure 6:
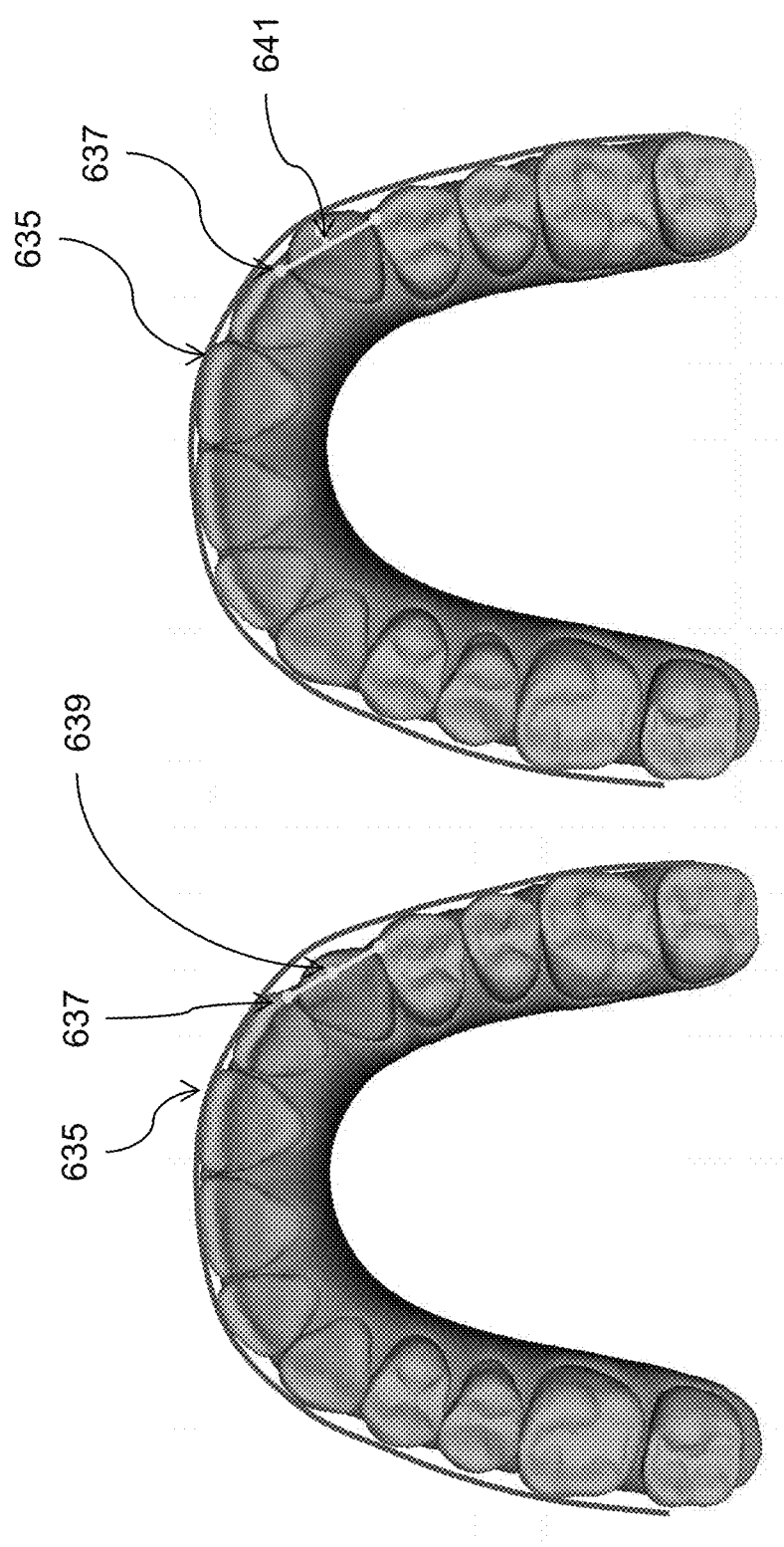
FIG. 6 provides an example of a straight line placement for an erupting tooth in the left image and an example of an arch line placement for an erupting tooth according to one or more embodiments of the present disclosure in the right image.

FIG. 6 provides an example of a straight line placement for an erupting tooth in the left image and an example of an arch line placement for an erupting tooth according to one or more embodiments of the present disclosure in the right image. In the prior art implementation illustrated in the left image of FIG. 6, virtual geometries were placed in the arch based on a tooth placement algorithm where the virtual geometry was positioned in the mid-point 639 of a straight line 637 connecting the contact points (i.e., the points at which two adjacent teeth contact each other or would contact each other if they were moved into contact) of two adjacent teeth. Therefore, prior art virtual geometry placement algorithm can result in inherent errors where virtual geometries may be positioned more lingually than where the naturally erupting tooth would be. This shortcoming can be more pronounced with canines than premolars, since canine location in the arch typically is in the most convex curvature area.

Embodiments of the present disclosure can utilize a placement methodology that is based on an arch form analysis (i.e., accounting for the arched shape of the jaws of a patient and the arched pattern in which the teeth are positioned thereon) rather than a straight line methodology to reduce such inherent placement errors. The right image of FIG. 6 provides such an embodiment. In the right image, the arch form is illustrated by line 635. In such an embodiment, instead of taking the mid-point of a straight line 637, the methodology takes into account the location of the arch form 635.

In some embodiments, the arch form concept is incorporated into the computation used to position teeth. For example, historical data from one or more patients (in some instances, this analysis can include, for example, tens, hundreds, thousands, or millions of patients) can be analyzed and a distance or numerical value, between a naturally erupted tooth position and a tooth position placed at the mid-point of a straight line, can be determined. This predetermined distance or amount can then be applied to any patient and used to adjust the patient's tooth such that it gets closer to the arch form.

In such embodiments, the arch form information can be utilized to identify, where the tooth will be positioned such that it contacts the two adjacent teeth (e.g., that dots at the end of the straight line 637) and the line of the arch form (e.g., at point 641). As can be seen from this illustration, the tooth is therefore moved out a distance from mid-point of the straight line which should place the tooth in a more desirable position.

Figure 7:
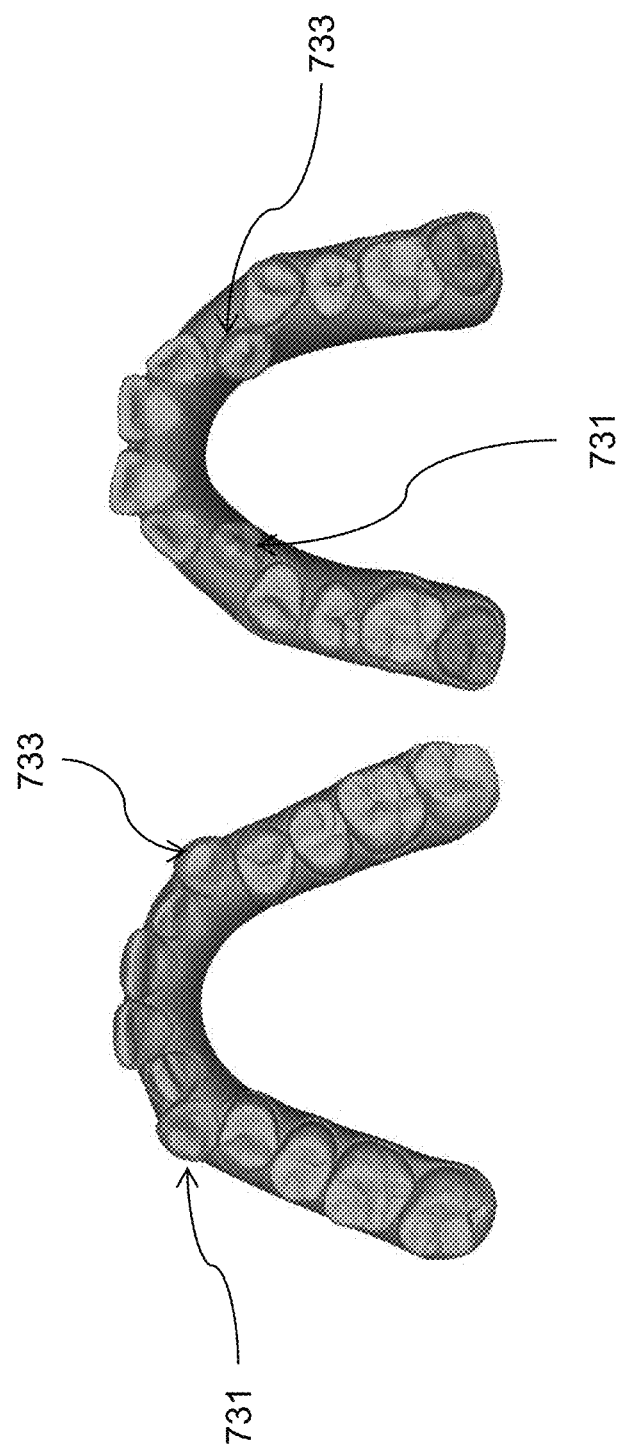
FIG. 7 illustrates examples of erupted canine teeth that are positioned with buccal displacement and palatal displacement.

FIG. 7 illustrates examples of canine teeth that are naturally erupted with buccal displacement and palatal displacement. In FIG. 7, the images illustrate the different positions of two teeth 731 and 733. The left image provides an example of buccally displaced canine teeth and the the right image provides an example of palatally displaced canine teeth. Although these teeth are erupted, FIG. 7 is provided to allow the reader to better understand the concepts of buccal displacement and palatal displacement.

In some situations, the available arch space is not sufficiently large for the erupting tooth. In such situations, the normal eruption of the tooth can be hindered such that the tooth may not erupt into a location along the arch form, as shown in the examples of FIG. 7.

Therefore, the tooth may erupt at deviated locations to avoid collision with neighboring teeth, resulting in namely buccal displacement or palatal displacement of the erupting tooth, as defined in the current disclosure. As used herein, buccal displacement occurs when a tooth erupts in a more buccal position than its adjacent teeth and/or arch form, and palatal displacement occurs when a tooth erupts in more lingual position than its adjacent teeth and/or arch form. Such displacements may become a challenge for tooth placement algorithms and therefore, a treatment professional may have to provide input to make sure that the dental model accurately represents the patient's dentition.

In such situations, various embodiments of the present disclosure can be utilized to use available space size in the arch and the predicted dimension of erupting tooth in a single- or multivariate regression model (e.g., a buccal displacement canine (BDC) prediction model) to determine a potential displacement magnitude of the erupting tooth for buccally displaced canines in upper and/or lower jaws. The potential displacement magnitude can be determined, for example, by determining the difference in available space size and predicted tooth Mesioddistal (MD) width as a first regressor in the BDC prediction model. The larger the Buccolingual (BL) width of erupting tooth is, the more pronounced the buccal-displacement may be. Therefore, the predicted BL width of the erupting tooth can be used as an additional regressor in the BDC prediction model.

Once it is decided that a buccally displaced eruption of one of the patient's canines is expected from clinical assessment, the BDC prediction model can, for example, be additionally applied to the tooth placement algorithm to improve accuracy of virtual geometry location for an erupting tooth. Clinical assessment can be made by treatment professionals, for example, by using gingival palpation, visual inspection, X-ray, CBCT scan, etc. In this manner, the displacement of one or more teeth can be accounted for in design of one or more of the dental appliances fabricated for a patient.

As discussed above, appliances according to the present disclosure can include, in some embodiments, a plurality of incremental dental position adjustment appliances. The appliances can be utilized to incrementally implement a treatment plan such as by affecting incremental repositioning of individual teeth in the jaw, among other suitable uses. In some implementations, appliances can be fabricated according to a virtual dental model that has had positions of a number of teeth adjusted according to one or more embodiments of the present disclosure.

Appliances can also include any positioners, retainers, and/or other removable appliances for finishing and/or maintaining teeth positioning in connection with a dental treatment. These appliances may be utilized by the treatment professional in performing a treatment plan. For example, a treatment plan can include the use of a set of appliances, created according to models described herein.

An appliance can, for example, be fabricated from a polymeric shell, and/or formed from other material, having a plurality of cavities therein. The cavities can be designed (e.g., shaped) to receive one or more teeth and/or apply force to reposition one or more teeth of a jaw from one teeth arrangement to a successive teeth arrangement. The shell may be designed to fit over a number of, or in many instances all, teeth present in the upper or lower jaw.

A cavity can be shaped to mate with a particular tooth. For example, a particular cavity can be shaped to mate with three surfaces of a corresponding tooth to be received therein. The cavity may be slightly out of alignment with a current configuration of the particular tooth (e.g., to facilitate aligning the particular tooth to a desired configuration), but the cavity can generally conform to the shape of the particular tooth such that there is not much space between the cavity and the particular tooth when the appliance is worn.

As used herein, a "first stage" does not necessarily mean the original stage of a treatment plan, but is a relative term with respect to other stages. For example, the "first stage" may be a second stage of a 25 stage treatment plan, while the "second stage" may be a tenth stage of the 25 stage treatment plan, with the "third stage", for example, being a 15th stage of the 25 stage treatment plan, and the "fourth stage" may be a 24th stage of the 25 stage treatment plan.

Although not specifically illustrated, in some embodiments, for a particular stage in a treatment plan, both an upper appliance (an appliance designed to fit over teeth of a user's upper jaw) and lower appliance (an appliance designed to fit over teeth of a user's lower jaw) can be designed to interface with each other.

Figure 8:
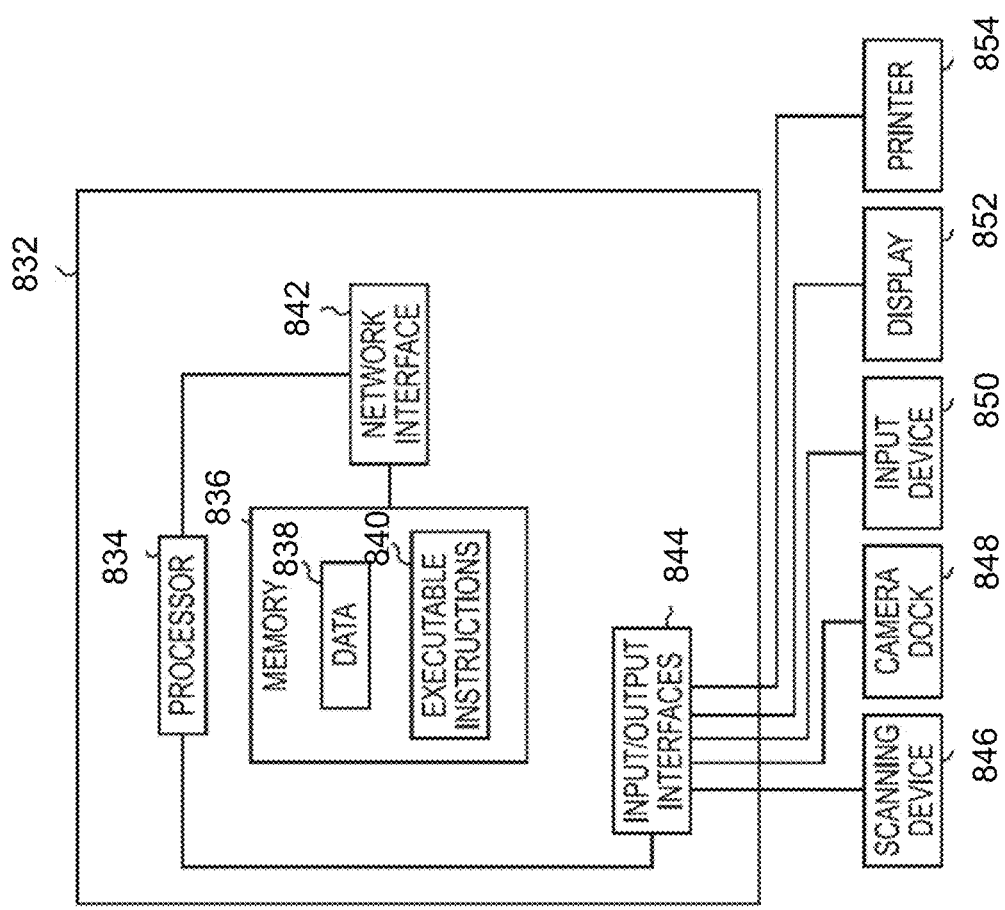
FIG. 8 illustrates a system for treatment planning according to one or more embodiments of the present disclosure.

FIG. 8 illustrates a system for treatment planning according to one or more embodiments of the present disclosure. A number of embodiments of the present disclosure include instructions that are executable by a processor (e.g., software), which can be fixed in a non-transitory computing device readable medium, to model, for example, a user's jaws (e.g., including teeth, roots, gingiva, and/or supporting structure, etc.).

The instructions can be executed to create and/or modify a treatment plan to incrementally adjust the user's teeth and/or bite, among other adjustments, via application of a series of appliances as described herein. The instructions can be executed to provide modified models of the user's jaws for each of the various stages of the treatment plan for fabrication (e.g., via rapid prototyping such as stereolithography) of physical models corresponding to the virtual models. The physical models can be used for the fabrication (e.g., via thermoforming) of appliances thereover. In some embodiments, executable instructions can create the appliances directly from the virtual model without the use of a mold.

FIG. 8 illustrates a system for treatment planning according to one or more embodiments of the present disclosure. In the system illustrated in FIG. 8, the system includes a computing device 832 having a number of components coupled thereto. The computing device 832 includes a processor 834 and memory 836.

The memory 836 can include various types of information including data 838 and executable instructions 840, as discussed herein. The memory can be a non-transitory computing device readable medium having instructions stored thereon that are executable by a processor to cause a computing device perform various functions as described herein. Additionally, memory can hold data that can be used in the performance of the executable instructions (e.g., data regarding the dimensions of a neighboring tooth).

Memory and/or the processor may be located on the computing device 832 or off the device, in some embodiments. As such, as illustrated in the embodiment of FIG. 8, a system can include a network interface 842. Such an interface can allow for processing on another networked computing device or such devices can be used to obtain information about the patient or executable instructions for use with various embodiments provided herein.

As illustrated in the embodiment of FIG. 8, a system can include one or more input and/or output interfaces 844. Such interfaces can be used to connect the computing device with one or more input or output devices.

For example, in the embodiment illustrated in FIG. 8, the system includes connectivity to a scanning device 846, a camera dock 848, an input device 850 (e.g., a keyboard, mouse, etc.), a display device 852 (e.g., a monitor), and a printer 854. The processor 834 can be configured to provide a visual indication of a virtual model on the display 852 (e.g., on a GUI running on the processor 834 and visible on the display 852). The input/output interface 844 can receive data, storable in the data storage device (e.g., memory 836), representing the virtual model (e.g., corresponding to the patient's upper jaw and the patient's lower jaw).

In some embodiments, the scanning device 846 can be configured to scan a physical mold of a patient's upper jaw and a physical mold of a patient's lower jaw. In one or more embodiments, the scanning device 846 can be configured to scan the patient's upper and/or lower jaws directly (e.g., intraorally).

The camera dock 848 can receive an input from an imaging device (e.g., a 2D imaging device) such as a digital camera or a printed photograph scanner. The input from the imaging device can be stored in the memory 836.

Such connectivity can allow for the input and/or output of virtual model information or instructions (e.g., input via keyboard) among other types of information. Although some embodiments may be distributed among various computing devices within one or more networks, such systems as illustrated in FIG. 8 can be beneficial in allowing for the capture, calculation, and/or analysis of information discussed herein.

The processor 834, in association with the memory 836, can be associated with data and/or application modules. The processor 834, in association with the memory 836, can store and/or utilize data and/or execute instructions to provide treatment planning that includes an attachment structure.

Such data can include the virtual model described herein (e.g., including a first jaw, a second jaw, a number of appliances, etc.). Such executable instructions can include instructions for attachment structure design and/or placement, force calculation, engagement force calculation, and/or treatment planning, among other functions.

Instructions for appliance design and/or cavity size, shape, and positioning can be configured to create at least one cavity into which an erupting tooth will be positioned on a virtual model of a patient's jaw. In some embodiments, the executable instructions can, for example, be executed to perform a method including to: receive, via a computing device, data representing a plurality of teeth, identify data indicating which of the plurality of teeth are unerupted or erupting, evaluate the data for tooth size information, predict size and orientation of the unerupted or erupting teeth after they have fully erupted using the tooth size information, generate new data representing the unerupted or erupting teeth in multiple states of eruption based upon the predicted size and orientation of the fully erupted teeth, and generate a series of incremental tooth arrangements with the new data to define a proposed orthodontic treatment based on the new data representing the unerupted or erupting teeth in multiple states of eruption.

In some embodiments, executable instructions can be utilized, for example, wherein evaluating the data for tooth size information includes obtaining dimensional data for at least one dimension of at least one of a tooth adjacent to the unerupted or erupting tooth or an opposing tooth to the unerupted or erupting tooth. Evaluating the data for tooth size information can also include determining a first projected dimension for the unerupted or erupting tooth based on the dimensional tooth data.

Generating new data representing the plurality of teeth in a fully erupted state can, for example, include determining a scaling factor for the first projected dimension of a cavity of a virtual dental appliance positioned to accommodate the unerupted or erupting tooth as the tooth erupts. As discussed above, the scaling factor can, for instance, be based on a calculation of available space in a corresponding dimension around the unerupted or erupting tooth and sized such that the unerupted or erupting tooth will not contact a surface of the cavity as the tooth erupts during a period of treatment. The period of treatment can, for example, be from a current state of the plurality of teeth through the end of a treatment plan or one period in a treatment plan that is divided into multiple, sequential periods of treatment, among other suitable periods of treatment.

FIG. 9 illustrates an example of a method embodiment of the present disclosure for creating a dental appliance having a cavity for an unerupted or erupting tooth. The method of FIG. 9 is utilized for defining an unerupted or erupting tooth during a proposed orthodontic treatment and includes identifying, via a computing device, whether a patient's arch contains an unerupted or erupting tooth, at block 960.

The method also includes, obtaining dimensional data for at least one dimension of at least one tooth of the patient, at block 962. Obtaining dimensional data for at least one dimension of at least one tooth of the patient can, for example, include obtaining dimensional data for at least one dimension of at least one of a tooth adjacent to the unerupted or erupting tooth or an opposing tooth to the unerupted or erupting tooth.

At block 964, the method provides, determining a first projected dimension for the unerupted or erupting tooth based on the dimensional tooth data. The method also provides that determining a scaling factor for the first projected dimension of a cavity of a dental appliance positioned to accommodate the unerupted or erupting tooth as the tooth erupts, at block 966. In some embodiments, the scaling factor can, for example, be based on a calculation of available space in a corresponding dimension around the unerupted or erupting tooth and sized such that the unerupted or erupting tooth will not contact a surface of the cavity as the tooth erupts during a period of treatment.

And, at block 968, creating the dental appliance configured to reposition at least one tooth of the patient, the dental appliance including the cavity sized according to the determined scaled first projected dimension for the unerupted or erupting tooth. The cavity sized according to the determined scaled first projected dimension for the unerupted or erupting tooth can, for example, be positioned to accommodate the unerupted or erupting tooth as the tooth erupts during the period of treatment.

As discussed herein the dental appliance configured to reposition at least one tooth of the patient can be a virtual dental appliance (e.g., for use in treatment planning and/or dental appliance design) or a physical dental appliance (e.g., to be worn by a patient to, for example, implement a portion or an entire treatment plan.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A dental appliance system, comprising:
a first appliance of a series of appliances designed to incrementally implement a treatment plan, comprising a first shell having a plurality of cavities therein designed to receive teeth of a jaw in a first stage of the treatment plan with at least one of the plurality of cavities being a cavity configured to accommodate virtual maximum dimensions, in three dimensions above the gingival line, of an unerupted or erupting tooth therein; and
a second appliance of the series of appliances, comprising a second shell having a plurality of cavities therein designed to receive teeth of the jaw in a second stage of the treatment plan the second shell having a cavity that corresponds with the cavity configured to accommodate virtual maximum dimensions of an unerupted or erupting tooth of the first shell and wherein the virtual maximum dimensions are calculated by taking the maximum dimensions of two or more virtual tooth geometry data sets of the same type of tooth.

2. The system of claim 1, wherein the cavities configured to accommodate the virtual maximum dimensions of an unerupted or erupting tooth include a gingival edge and wherein the gingival edge is oriented and shaped based upon a prediction of the orientation and shape of the gingiva that will be adjacent to the gingival edge according to each shell's respective treatment stage.

3. The system of claim 1, wherein the cavities configured to accommodate the virtual maximum dimensions of an unerupted or erupting tooth each differ in at least one of: size, shape, location, or orientation.

4. The system of claim 1, wherein the cavities configured to accommodate the virtual maximum dimensions of an unerupted or erupting tooth have at least one characteristic of: size, shape, location, or orientation based on data representing the unerupted or erupting teeth in multiple states of eruption that is based upon one or more tooth eruption prediction factors of at least one fully erupted tooth of a patient.

5. The system of claim 1, wherein the cavities configured to accommodate the virtual maximum dimensions of an unerupted or erupting tooth have at least one characteristic of: size, shape, location, or orientation based on data including at least one of: a size, shape, location, and orientation of a tooth adjacent to the unerupted or erupting tooth.

6. The system of claim 1, wherein the cavities configured to accommodate the virtual maximum dimensions of an unerupted or erupting tooth have at least one characteristic of: size, shape, location, or orientation based on data including at least one of: a size, shape, location, and orientation of an opposing tooth to the unerupted or erupting tooth.

7. The system of claim 1, wherein the cavities configured to accommodate the virtual maximum dimensions of an unerupted or erupting tooth have at least one characteristic of: size, shape, location, or orientation based on data including at least one of: a size, shape, location, and orientation of a tooth that is the same type of tooth to the unerupted or erupting tooth.

* * * * *